US009913923B2

(12) United States Patent
Brown et al.

(10) Patent No.: US 9,913,923 B2
(45) Date of Patent: Mar. 13, 2018

(54) DECONTAMINATION SYSTEM (71) Applicant: AEROCLAVE, LLC, Winter Park, FL (US)

(72) Inventors: Ronald D. Brown, Maitland, FL (US); David J. Robinson, Orlando, FL (US); James S. Amrhein, Oviedo, FL (US)

(73) Assignee: Aeroclave, LLC, Winter Park, FL (US)

( * ) Notice: Subject to any disclaimer, the term of this patent is extended or adjusted under 35 U.S.C. 154(b) by 78 days.

(21) Appl. No.: 14/831,097

(22) Filed: Aug. 20, 2015

(65) Prior Publication Data

US 2016/0051715 A1 Feb. 25, 2016

Related U.S. Application Data (60) Provisional application No. 62/040,173, filed on Aug. 21, 2014.

(51) Int. Cl.
*A61L 2/22* (2006.01)
*A61L 2/18* (2006.01)
*A61L 9/14* (2006.01)

(52) U.S. Cl.
CPC .............. *A61L 2/22* (2013.01); *A61L 2/186* (2013.01); *A61L 9/14* (2013.01); *A61L 2202/15* (2013.01); *A61L 2202/16* (2013.01); *A61L 2202/25* (2013.01)

(58) Field of Classification Search
CPC .................. A61L 2/00; A61L 2/22; A61L 9/00
See application file for complete search history.

(56) References Cited

U.S. PATENT DOCUMENTS

| | | | | |
|---|---|---|---|---|
| 3,744,719 A | * | 7/1973 | Wallick | B05B 15/064 169/25 |
| 6,343,425 B1 | | 2/2002 | Sias et al. | |
| 6,550,487 B1 | * | 4/2003 | Duckett | A61L 2/22 134/108 |
| 6,706,243 B1 | | 3/2004 | Sias et al. | |
| 6,770,150 B1 | * | 8/2004 | Duckett | A61L 2/18 134/10 |
| 6,969,487 B1 | | 11/2005 | Sias et al. | |
| 7,008,592 B2 | | 3/2006 | Sias et al. | |
| 7,138,087 B1 | * | 11/2006 | Malkin | A61B 1/123 422/1 |
| 7,459,133 B2 | | 12/2008 | Swank | |
| 7,582,257 B2 | | 9/2009 | Bedard et al. | |
| 7,622,074 B2 | | 11/2009 | Mielnik | |

(Continued)

FOREIGN PATENT DOCUMENTS

EP 1116664 7/2001

*Primary Examiner* — Regina M Yoo
(74) *Attorney, Agent, or Firm* — Robert L. Wolter; Beusse, Wolter, Sanks & Maire PLLC (57) ABSTRACT

A system for decontaminating an enclosed area includes a reservoir containing a disinfectant solution therein. One or more pumps are in fluid communication with the reservoir. One or more ports are operatively connected to the reservoir or operatively connected to an enclosed area to be decontaminated or operatively connected to the reservoir and to an enclosed area to be decontaminated. One or more connector assemblies are removably attachable to the one or more ports to provide fluid flow communication between the disinfectant solution source and the enclosure to be decontaminated.

20 Claims, 7 Drawing Sheets

(56) References Cited

U.S. PATENT DOCUMENTS

| | | |
|---|---|---|
| 7,780,909 B2 | 8/2010 | Sparks |
| 7,790,104 B2 | 9/2010 | Adams |
| 7,837,687 B2 * | 11/2010 | Harp ................. A61B 17/1624 |
| | | 606/85 |
| 2005/0031486 A1 | 2/2005 | Mole et al. |
| 2006/0008379 A1 | 1/2006 | Mielnik et al. |
| 2006/0089090 A1 * | 4/2006 | Johnson .................... B24C 3/06 |
| | | 451/40 |
| 2009/0226241 A1 * | 9/2009 | McEwen ................ A46B 9/025 |
| | | 401/268 |
| 2011/0091358 A1 | 4/2011 | Chen |
| 2011/0092967 A1 * | 4/2011 | Harvey-Poncelet ... A61B 18/02 |
| | | 606/21 |
| 2011/0165021 A1 | 7/2011 | Berentsveig et al. |
| 2012/0116403 A1 * | 5/2012 | Harp ................. A61B 17/1624 |
| | | 606/85 |
| 2013/0078153 A1 * | 3/2013 | Hill .......................... A61L 2/22 |
| | | 422/111 |
| 2015/0246151 A1 * | 9/2015 | Brown ..................... A61L 2/22 |
| | | 239/69 |

* cited by examiner

DECONTAMINATION SYSTEM

CROSS-REFERENCE TO RELATED APPLICATIONS

This application claims the benefit of U.S. Provisional Application No. 62/040,173 filed Aug. 21, 2014, and is incorporated herein by reference in its entirety.

BACKGROUND OF THE INVENTION

The present invention relates to decontamination systems that generate a mist, fog or spray from a liquid disinfectant solution to sanitize surfaces within a confined area. More specifically, the invention relates to such systems that are on-board a vehicle.

Vehicles such as ambulances, fire-rescue vehicles, law enforcement vehicles etc., and the interior and exterior surfaces of such vehicles, at times may be exposed to harmful viruses, bacteria, chemicals and antimicrobrial compounds. Accordingly, it is necessary to sanitize and decontaminate the vehicles to minimize prevent the operators or occupants of the vehicles from being exposed to these harmful elements.

Systems have been developed that generate a decontaminant spray or fog applied to internal and external surfaces of a vehicle. One such system has been developed by Aero-Clave, LLC (Winter Park, Fla.) and is sold under the brand name PADS (Portable Asset Decontamination System). PADS is a chamber that is large enough for a vehicle to enter. A disinfectant solution source and compressed air are provided in fluid communication to a plurality of nozzles spaced apart in the room. PADS also includes a control system to control pumps, valves and an air compressor to deliver the disinfectant solution to the nozzles at timed intervals to inject the disinfectant solution in a spray or fog form. A vehicle is driven in the chamber and the doors and/or windows are opened and the disinfectant in spray or fog form is distributed through the nozzles and throughout the room to disinfectant interior and exterior surfaces of the vehicle.

AeroClave has also developed a portable unit that includes a container within which a reservoir containing a disinfectant solution, an air compressor, pumps and a controller are housed. The air compressor and pumps are within a housing in the container and the housing has a top cover that has portals to which nozzles can be removable attached. Alternatively, hoses with a nozzle at one end can be attached to the portals and the nozzles can be held by hand to apply disinfectant to surfaces of a vehicle or a room, or the nozzles may be placed on a stand. As with PADS, the controller can programmed to control delivery of the disinfectant solution for timed intervals to deliver a specified volume of disinfectant solution depending on the size of the surface area to be decontaminated or the volume of a room or interior of a vehicle to be decontaminated.

BRIEF DESCRIPTION OF THE INVENTION

The present invention relates to decontamination systems that generate a mist, fog or spray from a liquid disinfectant solution to sanitize surfaces within a confined or enclosed area. Embodiments of the invention provide a quick connect/disconnect between the disinfectant solution source and an enclosed area to be decontaminated.

A system for decontaminating an enclosed area comprises a decontamination unit including a reservoir containing a disinfectant solution and a supply of pressurized air. A nozzle mounted within the enclosed area to be decontaminated. One or more ports are in fluid communication with the reservoir and the supply of pressurized air, and/or the nozzle, wherein the one or more ports includes at least two fluid inlet portals or at least two fluid outlet portals.

One or more connector assemblies are operatively connectable to the reservoir and the pressurized air supply and/or the one or more ports. In an embodiment, the one or more connector assemblies may include an umbilical housing having a first fluid line through which the disinfectant solution flows from reservoir to the nozzle and a second fluid line through which pressurized air flows from the supply of pressurized air to the nozzle. Electrical lines may be housed in the umbilical housing and connected to a controller or power source on the decontamination unit. A connector assembly may further comprise a connector head at an end of the umbilical housing wherein the connector head is configured for removable coupling to the one or more ports and the inlet or outlet fluid portals. The connector head may also include one or electrical leads or connectors to connect to electrical leads or connectors at a port to supply electricity to components such as a light or audible component to activate the components to generate signals relative to a decontamination operation.

The invention disclosed herein may be particularly useful for sterilizing or decontamination of spaces and surfaces within rooms that are exposed to harmful viruses, bacteria, etc. Accordingly, the decontamination system may be beneficial for buildings or structures having a large number of rooms and in which a large number people may work or visit. Such buildings may include for example police/fire department buildings, hospitals, mass transit facilities, hotels, cruise ships, etc.; however, the subject invention is not necessarily limited to these types of buildings. Moreover, embodiments of the invention may be used to decontaminate enclosed areas of vehicles such as ambulances, first response vehicles or transportation assets such as train cars, buses etc.

DESCRIPTION OF THE INVENTION

A more particular description of the invention briefly described above will be rendered by reference to specific embodiments thereof that are illustrated in the appended drawings. Understanding that these drawings depict only typical embodiments of the invention and are not therefore to be considered to be limiting of its scope, the invention will be described and explained.

Figure 9:
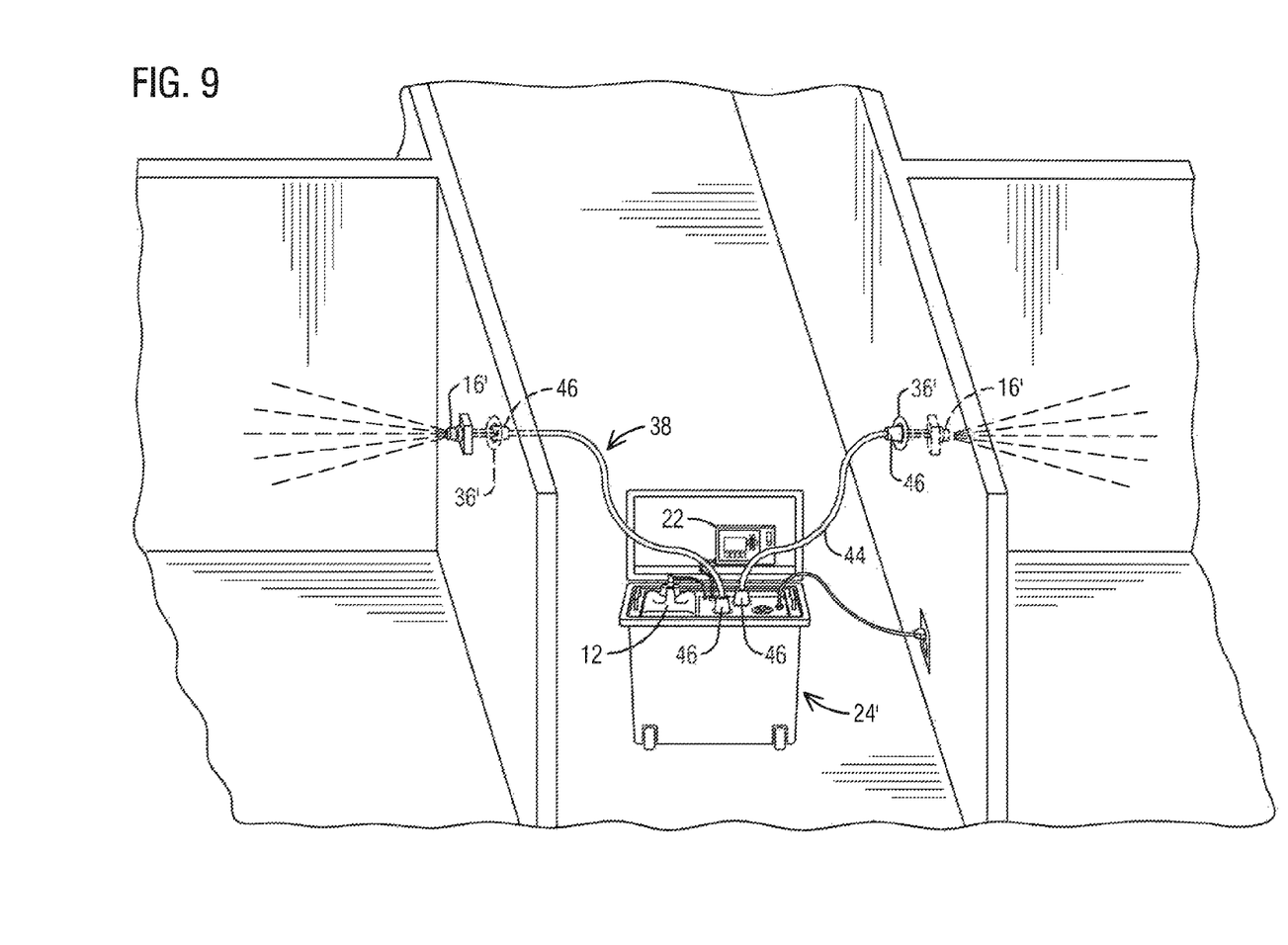
FIG. 9 is an elevational view of a decontamination unit connected to portals on interior walls of a building.

With respect to FIGS. 1-7, embodiments of decontamination systems 10 are shown for use in connection with decontaminating an interior space of a vehicle 18. The embodiment of FIG. 9 shows the use of the decontamination system 10 in connection with decontaminating rooms of a building. Accordingly, the decontamination system may be used to decontaminant virtually any enclosed area. The term enclosed area herein is intended to mean any partially or completely enclosed area that is defined by one or more walls, a floor and/or a ceiling and/or roof.

As shown, the system 10 includes a reservoir 12 in which a disinfectant solution is stored. While the invention is not limited to any one particular type of disinfectant solution containing an effective disinfecting amount of a sterilant or disinfectant, disinfectant solutions that may be used with the subject invention may contain oxidizing agents such as acidified sodium chlorite compounds (such as chlorine dioxide), hydrogen peroxide, and sodium hypochlorite (bleach). Another disinfectant that may be used is chlorhexidine or other chlorine based compounds. Again, these disinfectants and disinfectant solutions are provided by way of example only, and the invention is not limited to a particular type of disinfectant solution.

Figure 5:
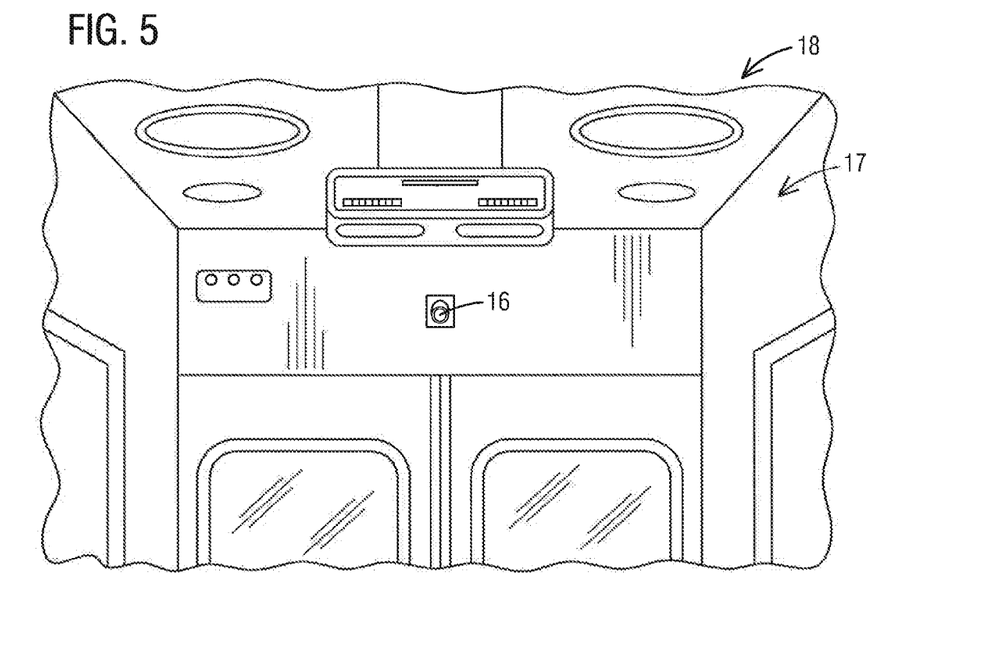
FIG. 5 is a perspective view of an interior of the vehicle of FIG. 1 illustrating a spray nozzle mounted therein for distribution of a disinfectant.

In embodiments in which the disinfectant solution is sprayed into an interior space or an enclosed area, the system 10 may also include one or more air compressors 14 (not shown in FIGS. 1-3, but shown in FIG. 7) that deliver pressurized air to a nozzle 16 (FIG. 5). The nozzle 16 depicted in FIG. 5 is mounted in an enclosed area 17 of the vehicle 18 to be decontaminated. While the nozzle 16 can be a component of an assembly that includes other components such as sensors, signal lights, audible devices, etc. While only a single nozzle 16 is shown, multiple nozzles may be used with the system 10.

In addition, one or more pumps 20 (FIG. 7), which are in fluid communication with the reservoir 12, deliver the disinfectant solution from the reservoir 12 to the nozzle 16. Accordingly, one or more fluid lines provide fluid communication from reservoir 12 to the pump(s) 20 and to the nozzle 16. Embodiments may include multiple pumps each pump being associated with a corresponding nozzle, in which case smaller pumps, such as peristaltic pumps, may be used. Alternatively, larger pumps may be used to service multiple nozzles. An example of a peristaltic pump that may be used with system 10 is a 30 ml/min. pump sold by Gardner Denver Thomas.

The system 10 may further comprise a programmable controller 22 to control the activation and deactivation of the air compressor 14 and pumps 20 to deliver the disinfectant solution on demand. In addition, a sensor (not shown) may be mounted in the interior space being contaminated to detect levels of a disinfectant compound associated with the solution. In the example of a hydrogen peroxide disinfectant solution, the sensor detects levels of hydrogen peroxide in an interior space of the vehicle 18. The sensor is preferably in signal communication with the controller 22, which may be programmed to send various commands or electrical signals in response to the level of disinfectant compound detected to control operations of the decontamination system 10. The controller 22 may be configured or programmed, for example, to issue commands or signals such as to activate lights or audible warnings or indicators when the concentration of the disinfectant remains at or above a threshold or drops below the threshold.

Figure 1:
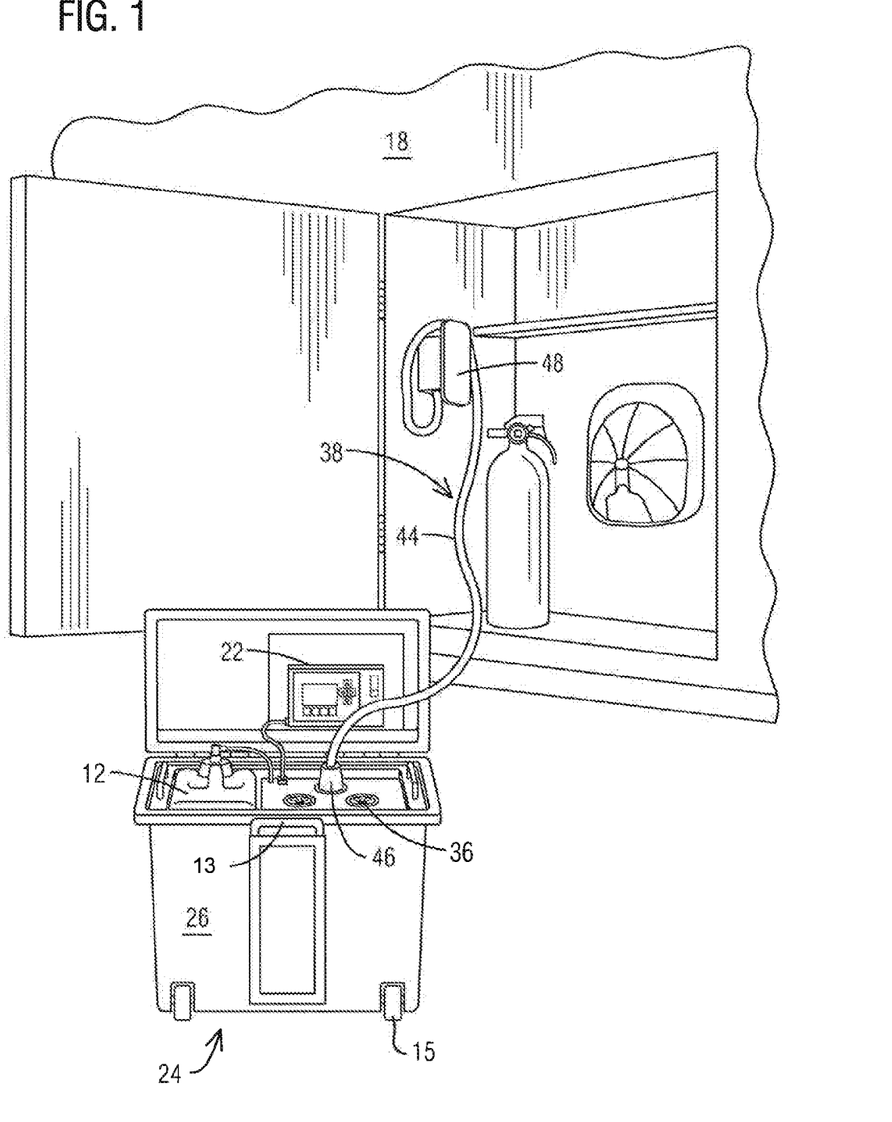
FIG. 1 is a perspective view of a fire-rescue vehicle with a connector assembly providing fluid flow communication between a decontamination unit and an interior space of the vehicle.
Figure 2:
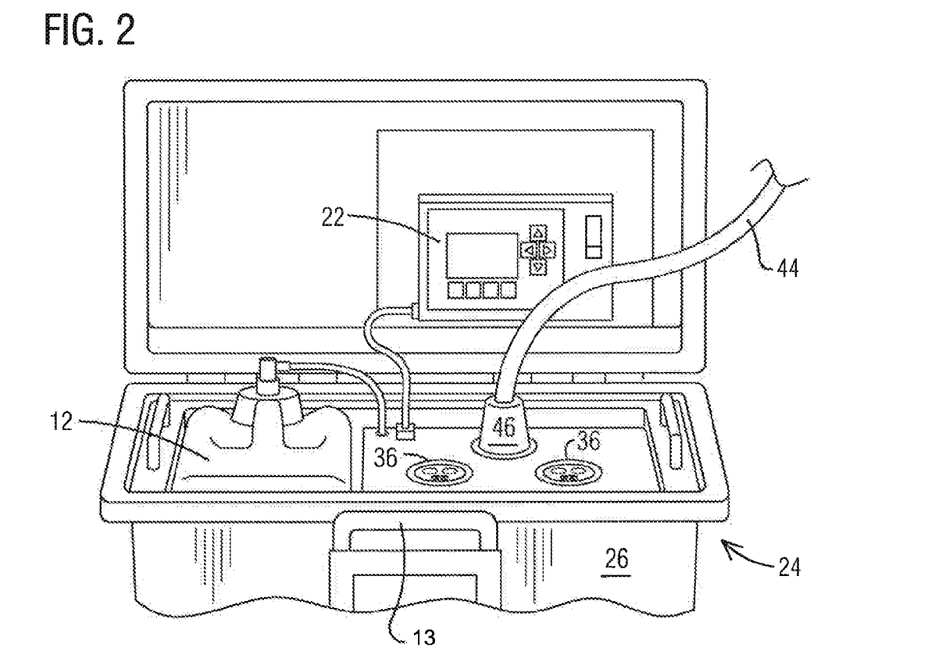
FIG. 2 is a perspective view of the decontamination unit of FIG. 1.
Figure 3:
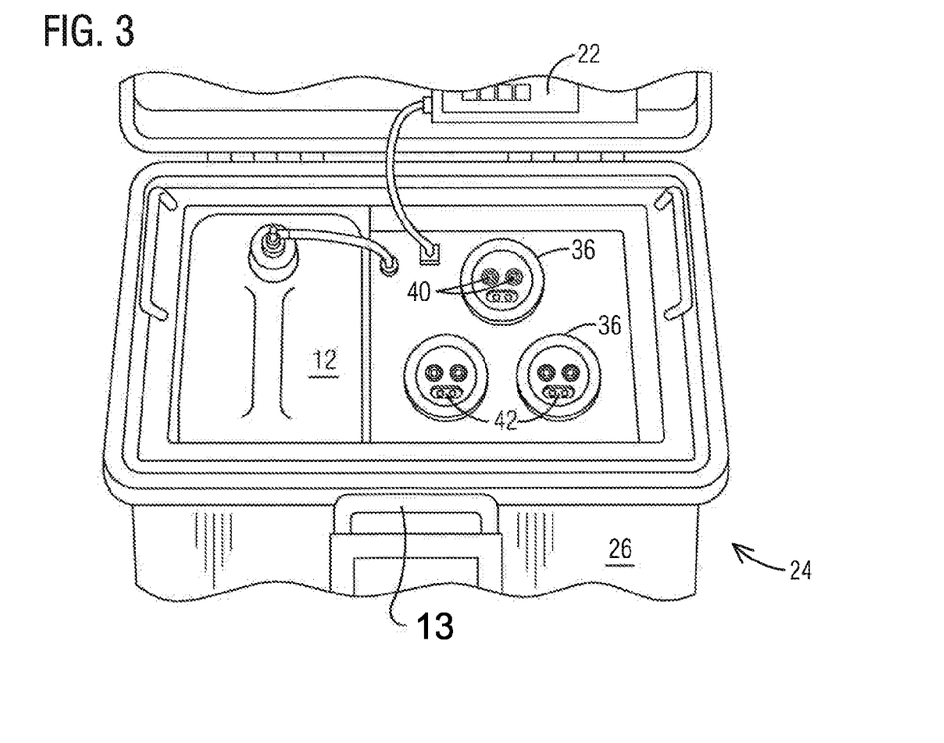
FIG. 3 is a top view of the decontamination unit of FIG. 1 showing a plurality of connector ports thereon
Figure 4:
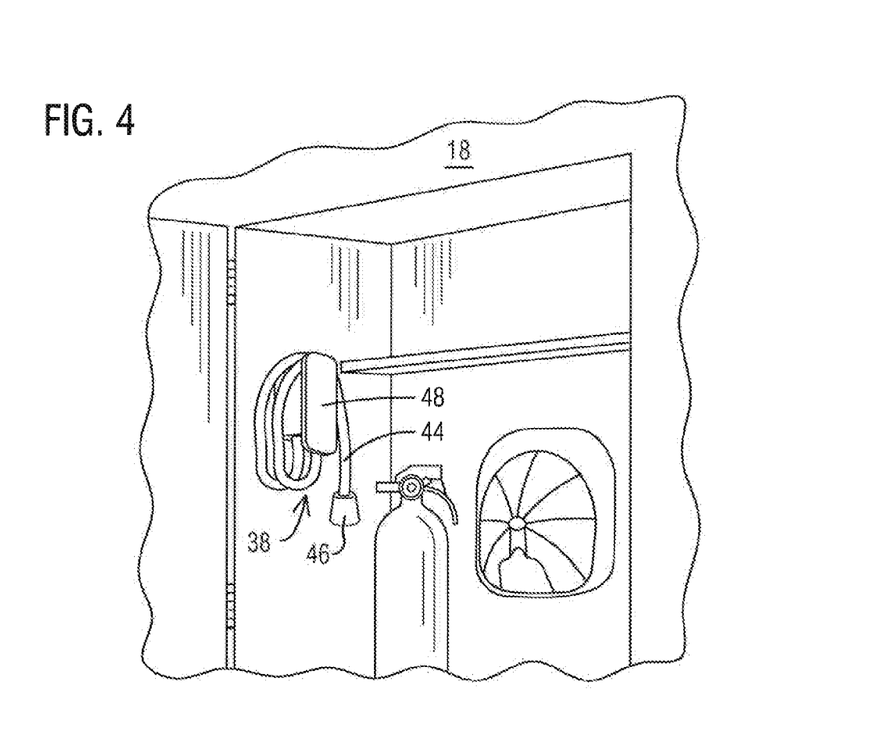
FIG. 4 is a perspective view of the fire-rescue vehicle of FIG. 1 with the connector assembly including an umbilical and connector head.
Figure 7:
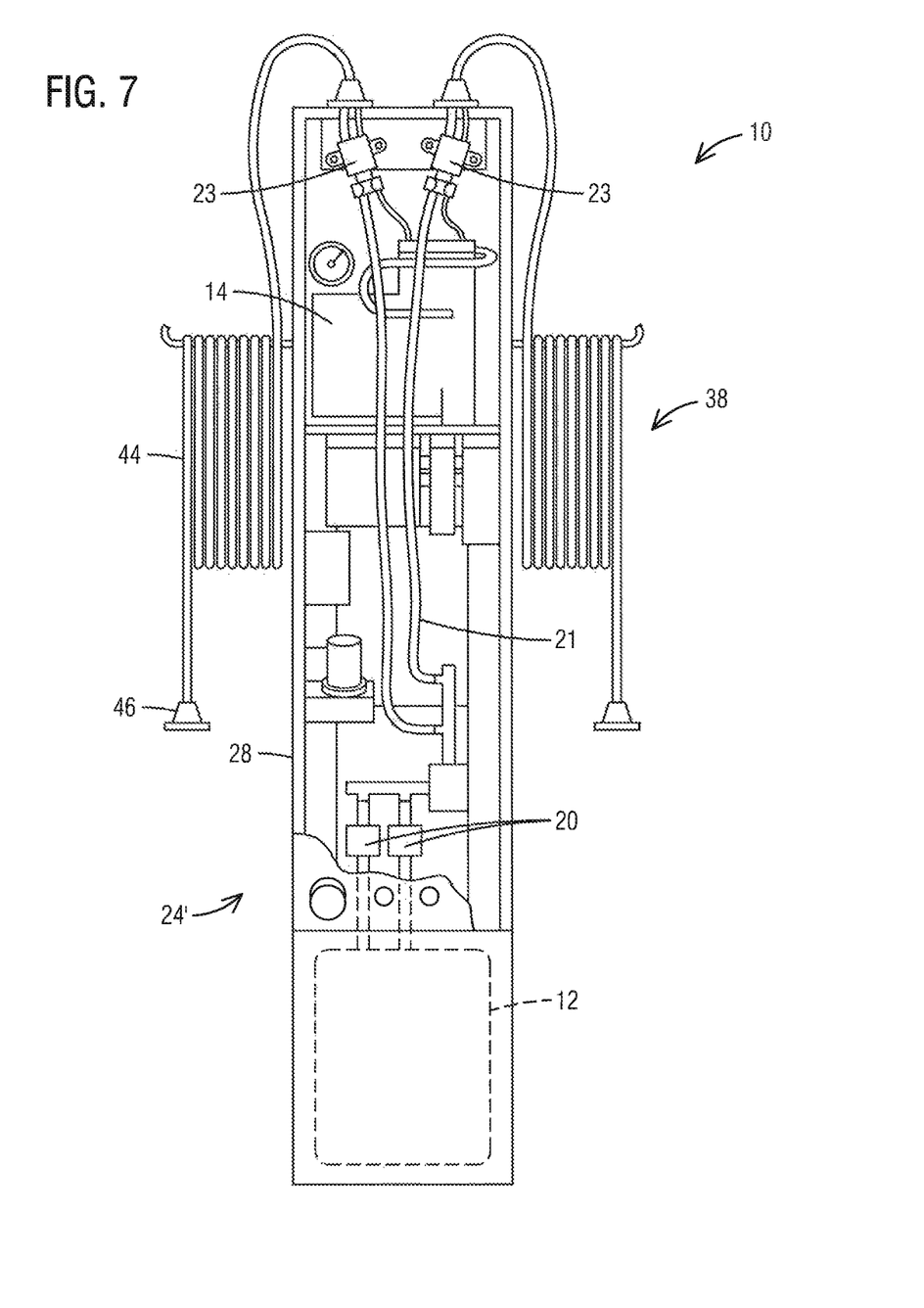
FIG. 7 is an elevational view of a wall mounted decontamination unit with connector assemblies

In the embodiment shown in FIGS. 1-3, the reservoir 12, air compressor 14, pumps 20 and controller 22 are positioned on or in a casing or housing 26, which may be portable, and together may be referred to as the decontamination unit 24. As shown, the housing 26 includes wheels 15 and a retractable handle 13 to move the unit 24 including housing 26 and components therein for positioning next to the vehicle 18. In another embodiment the system may include a stationary housing. By way of example, as shown in FIG. 7, a housing 28 may be positioned on a floor of a building or mounted to a wall of a building. As further shown, the decontamination unit 24' of FIG. 7 includes the above mentioned pumps in fluid communication with the reservoir 12, fluid lines 21 and solenoid valves 23 to deliver disinfectant solution to an interior space via the below-described connector assemblies.

Figure 6:
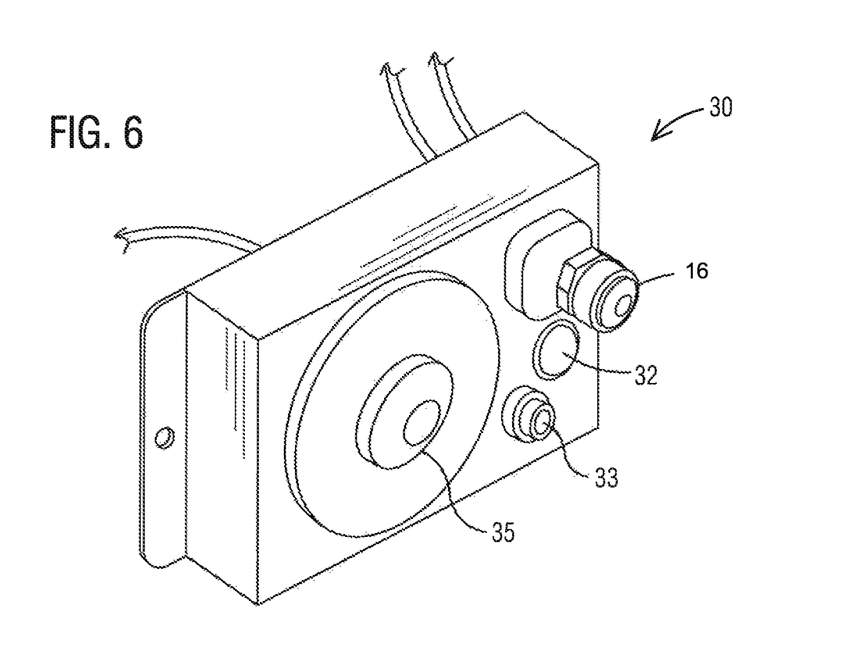
FIG. 6 is a perspective view of a nozzle assembly.

An embodiment of the invention may include a nozzle assembly 30 as depicted in FIG. 6 and may be mounted to the vehicle in the interior space of the vehicle to be decontaminated. As shown, the nozzle assembly 30 includes various components that perform different functions associated with the operation of the decontamination system 10. As shown in FIG. 6, the assembly 30 comprises a nozzle 16 through which the disinfectant solution is delivered under pressure with compressed air to atomize the solution in order to generally, uniformly disperse the solution throughout the interior space to be decontaminated. Embodiments may include multiple nozzles in fluid communication with the reservoir 12.

Other components on the assembly 30 may include a warning light 32 in signal communication with the controller 22. The assembly 30 may also include or alternatively include a sensor tube 33 which is in fluid communication with a vacuum pump and sensor at the decontamination unit 24. When activated the vacuum pump draws air in the interior space through the sensor tube 33 and to the sensor to detect levels of the effective decontaminant chemical of the solution delivered to the interior space. The sensor (not shown) and warning light 32 are in signal communication the controller 22 so that the light 32 may be activated or deactivated in response to levels of the decontaminating compound detected in the enclosed. Alternatively, a sensor may be mounted within the interior space instead of mounted on the assembly 30. The assembly 30 may also include a motion detector 35 to detect the presence or absence of anyone in the interior space before a decontamination operation is conducted.

As further shown in FIGS. 1-3, the system 10 may comprise one or more ports 36 operatively connected to the reservoir 12, and one or more connector assemblies 38 removably attachable to the one or more ports 36 to provide fluid flow communication between the reservoir and an interior space or enclosed area to be decontaminated, or fluid flow communication between the reservoir 12 and a nozzle 16. The connector assemblies 38 provide fluid flow communication between the reservoir 12 and nozzle 16. In the embodiment, shown in FIGS. 1-3, the port 36 is affixed to the casing 26, and the port 36 is in fluid flow communication with the pump 20 and reservoir 12 via fluid flow lines (not shown). As shown in more detail in FIG. 3, the port 36 includes first fluid outlet 41 through which the disinfectant solution flows to the nozzle 16 and a second fluid outlet 43 through which pressurized air flows to the nozzle 16. In addition, the port 36 may have electrical sockets 42 to receive electrical contact pins as described below in more detail.

A connector assembly 38 is provided at the vehicle 18 and includes an umbilical 44 and connector head 46 that connects to the port 36, to provide fluid flow communication between the reservoir 12, the air compressor 14 and the nozzle 16. Such connector assemblies may be purchased from Colder Products Company of St. Paul Minn. The connector head 46 includes male fluid couplers that connect to the above-referenced female couplers 40 to complete the fluid flow communication of the reservoir 12 and air compressor 14 to the nozzle 16.

Figure 10:
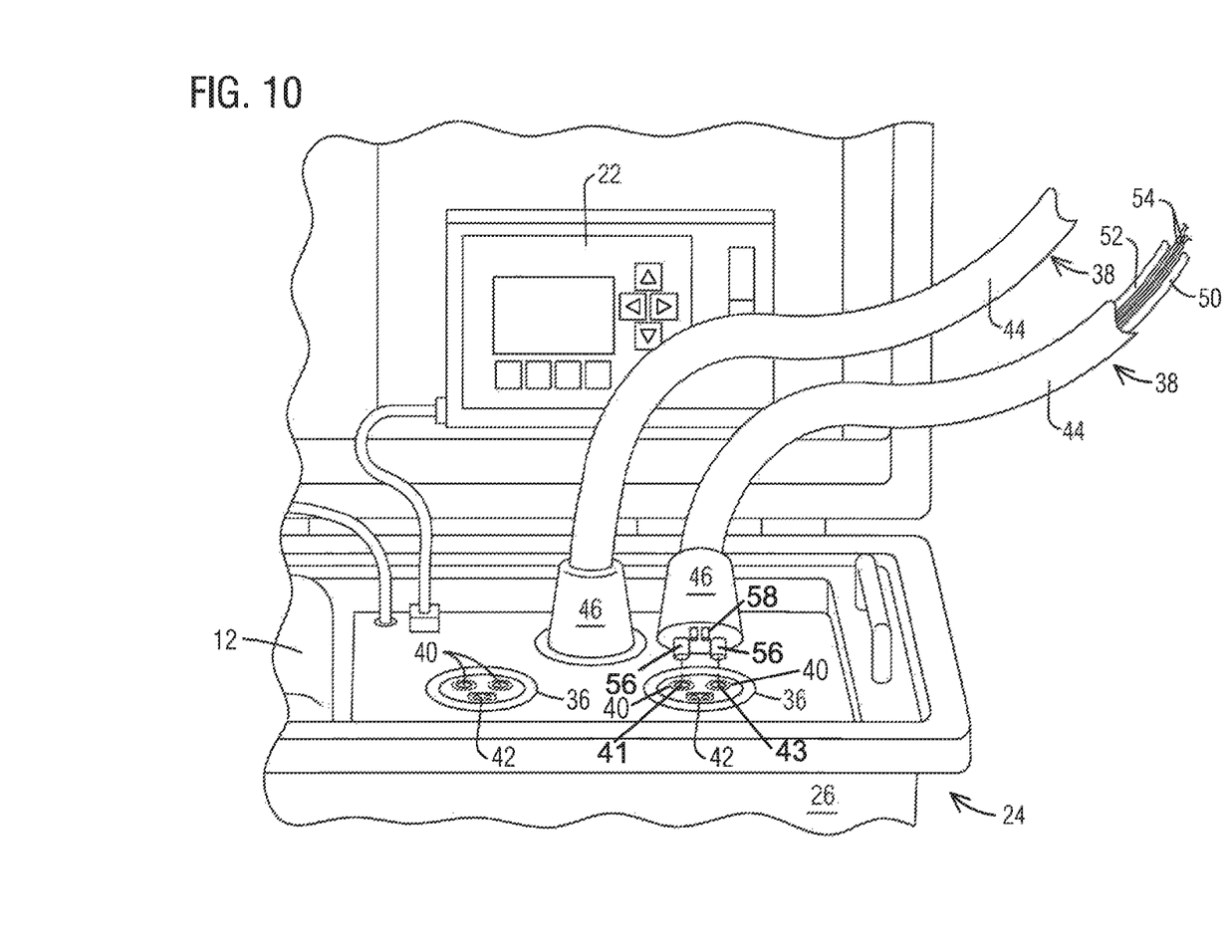
FIG. 10 is a perspective view of the decontamination system showing the fluid lines and electrical lines in an umbilical housing of connector assembly

As further shown in FIG. 10, The umbilical 44 includes a flexible housing through which fluid lines 50, 52 extend to the connector head 46 and male couplers to the nozzle 16 to provide the disinfectant solution and pressurized air at the nozzle 16 so the disinfectant solution is atomized at the nozzle 16 and is generally, uniformly dispersed to decontaminate surfaces in the area. The umbilical 44 may also include electrical lines 54 to transmit electrical signal to electronic components such as warning lights or sensor, for example.

Again with respect to FIGS. 3 and 10, the head 46 may include male couplers 56 to connect to below-described female couplers 40 at a port 36; however, the port 36 may have male couplings and the head 46 may have female couplings. In addition, the head 46 may have electrical leads 58 to connect to a socket 42 at a port 36.

In the embodiment shown in FIGS. 1-4, the umbilical 44 terminates at a junction box 48 that includes at least the disinfectant fluid line and compressed air line that continue on to the nozzle 16. To the extent that electronic components, such as sensors or warning lights are provided, the umbilical 44 may include electrical wiring leading to the junction box 48.

Figure 8:
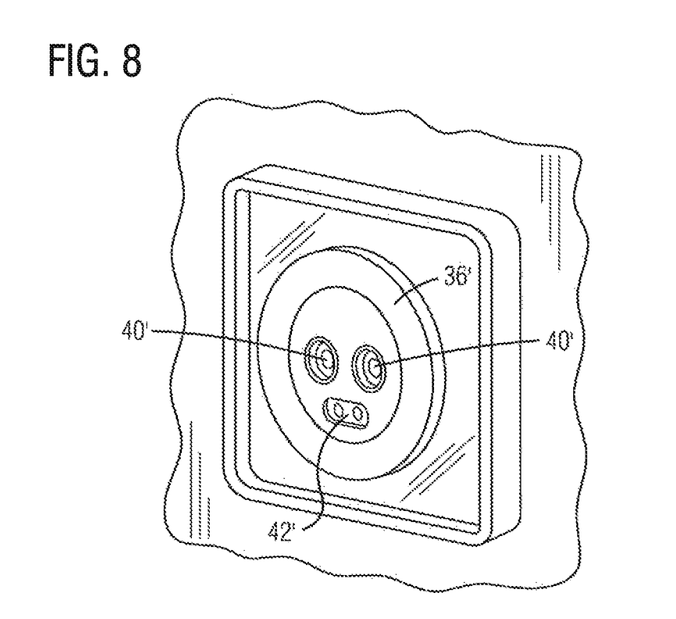
FIG. 8 is a perspective view of port mounted to a wall for connection to a decontamination unit to decontaminate an interior of a room.

While the embodiment shown in FIGS. 1-4 include a port 36 at the decontamination unit 24 and a single connector head 46 for the connector assembly 38, other embodiments may include two ports 36 including one port at the decontamination unit 24 and one port on the vehicle 18, or a port on a wall of an interior space to be decontaminated. A wall mounted port 36' is shown in FIG. 8 including female fluid couplers 40 and electrical sockets 42'. In such an embodiment, the connector assembly 38 will include an umbilical 44 with a connector head 46 at each end. In yet another embodiment, a port may be mounted to a wall of an interior space and the umbilical has a single connector head 46 at one end and the other end of the umbilical is fixed to a decontamination unit 24.

With respect to any of the above-described embodiments that may be used to decontaminate an interior space of a vehicle, the vehicle 18 is positioned and prepped for decontamination and the connector assemblies are plugged into the respective port(s) and the decontamination unit is activated. When the decontamination procedure is complete the connector assemblies are disconnected and stored as necessary. With respect to the embodiment shown in FIG. 1, the connector assembly is stored on the vehicle 18. For the embodiment shown in FIG. 7, the connector assemblies are stored on a rack on the housing 28 of the unit 24'. Alternatively, spring-loaded reels may be provided on which the umbilical of a connector is wound so the umbilical may be readily unwound to connect to a port for decontamination of an interior space.

As referenced above, the system 10 and decontamination units 24, 24' may be used to decontaminate rooms within a building. As illustrated in FIG. 9, ports 36' are mounted on interior walls 60 of a building; and ports 36 are affixed to the casing 26 of the decontamination unit 24. Accordingly, the connector assemblies 38 include connector heads 46 at both ends of the assemblies 38. The ports 36' on the walls 60 are positioned so that multiple connector assemblies 38 can he connected to the wall ports 36' at any one time. In this manner, multiple rooms can be simultaneously decontaminated. An operator of the unit 24 positions the unit in a hallway to access the wall ports 36. The connector assemblies 38 are plugged into the respect ports 36, 36', and the system is activated. Disinfectant solution and pressurized air are delivered to the nozzles 16' via fluid lines in the umbilical 44.

The controller 22 is preferably programmed to control the injection of disinfectant solution into the rooms for one or more timed intervals, and deactivate the injection of the disinfectant solution after the one or more timed intervals has elapsed. When a decontamination procedure is completed the connector assemblies 38 are unplugged or disconnected from the wall ports 36' and the unit 24 is moved to perform decontamination operations for one or more rooms. When all decontamination operations are complete the connector assemblies 38 are preferably disconnected from both ports 36, 36' and stored accordingly.

While certain embodiments of the present invention have been shown and described herein, such embodiments are provided by way of example only. Numerous variations, changes and substitutions will occur to those of skill in the art without departing from the invention herein. Accordingly, it is intended that the invention be limited only by the spirit and scope of the appended claims.

We claim:

1. A system for decontaminating an enclosed area, comprising:
    a reservoir containing a disinfectant solution therein;
    one or more pumps in fluid communication with the reservoir;
    a pressurized air source;
    one or more ports, each port comprising a first coupler and a second coupler, wherein the first coupler is operatively connected to the reservoir and the second coupler is operatively connected to the pressurized air source, or wherein the first coupler is operatively connected to an enclosed area to be decontaminated and the second coupler is operatively connected to the enclosed area to be decontaminated; and,
    one or more connector assemblies removably attachable to the one or more ports, each connector assembly comprising a first fluid line in fluid communication with the first coupler to provide fluid flow communication between the reservoir and the enclosed area to be decontaminated, and a second fluid line in fluid communication with the second coupler to provide fluid flow communication between the pressurized air source and the enclosed area to be decontaminated.

2. The system of claim 1, further comprising one or more nozzles mounted to an internal surface of the enclosed area to be decontaminated, each nozzle in fluid flow communication with; a port or a respective port of the one or more ports, a connector assembly or a respective connector assembly of the one or more connector assemblies, the pressurized air source, and the reservoir when the connector assembly or the respective connector assembly is connected to the port or the respective port, wherein the one or more nozzles comprise atomizing nozzles.

3. The system of claim 2, wherein each connector assembly of the one or more connector assemblies comprises an umbilical housing in which a respective first fluid line and a respective second fluid line are housed, and a respective connector head attached to a respective end of the umbilical housing and configured to cooperate with the one or more ports to provide fluid flow communication between the reservoir and a respective nozzle.

4. The system of claim 2, further comprising a nozzle assembly mounted to the internal surface of the enclosed area to be decontaminated and comprising the one or more nozzles, the nozzle assembly further comprising an electrical component, the one or more ports each comprising an electrical connector, each connector assembly of the one or more connector assemblies further comprising an electrical line configured to deliver electrical power to the electrical component and an electrical lead at an end of the electrical line configured to cooperate with the electrical connector.

5. The system of claim 4, wherein the electrical component comprises at least one of: a motion detector configured to detect motion in the enclosed area to be decontaminated; and a warning light.

6. The system of claim 2, further comprising:
a vacuum pump in fluid communication with the one or more ports;
a sensor in fluid communication with the vacuum pump and configured to detect a level of disinfectant;
a nozzle assembly mounted to the internal surface of the enclosed area to be decontaminated and comprising the one or more nozzles, the nozzle assembly further comprising a sensor tube opening;
wherein the nozzle assembly further comprises a third fluid line that provides fluid communication between the sensor tube opening and the sensor.

7. The system of claim 1, wherein the reservoir is a component of a mobile decontamination unit.

8. The system of claim 7, further comprising:
one or more atomizing nozzles mounted to an internal surface that defines an interior space of a vehicle;
wherein at least one port of the one or more ports is mounted to an exterior wall of the vehicle, wherein a respective first coupler of the at least one port is in fluid communication with a respective nozzle of the one or more atomizing nozzles, and wherein a respective second coupler of the at least one port is in fluid communication with the respective nozzle.

9. The system of claim 8, wherein the mobile decontamination unit comprises a cart with wheels and the reservoir is on the cart.

10. The system of claim 1, wherein the reservoir is a component of a stationary unit.

11. The system of claim 10, wherein the stationary unit comprises a housing mounted to a wall and the reservoir is in the housing and the one or more pumps are in the housing.

12. The system of claim 1, wherein the pressurized air source comprises an air compressor.

13. A system for decontaminating an enclosed area, comprising:
a decontamination unit including a reservoir containing a disinfectant solution;
a supply of pressurized air;
an atomizing nozzle mounted within the enclosed area to be decontaminated;
one or more ports that are in fluid communication with the reservoir and the supply of pressurized air, and/or the atomizing nozzle, wherein the one or more ports comprises at least two fluid inlet portals or at least two fluid outlet portals;
one or more connector assemblies operatively connectable to the reservoir and the supply of pressurized air and/or the one or more ports; wherein the one or more connector assemblies comprises an umbilical housing having a first fluid line through which the disinfectant solution flows from the reservoir to the atomizing nozzle and a second fluid line through which pressurized air flows from the supply of pressurized air to the atomizing nozzle; and,
the one or more connector assemblies further comprising a connector head at an end of the umbilical housing wherein the connector head is configured for removable coupling to the one or more ports and the at least two fluid inlet or outlet portals.

14. The system of claim 13, further comprising one or more pumps in fluid communication with the reservoir.

15. The system of claim 13, wherein in the one or more ports includes a port mounted to a wall defining at least a portion of the enclosed area.

16. The system of claim 15, wherein the port is mounted to a surface of the wall external to the enclosed area.

17. The system of claim 13, wherein the decontamination unit comprises a housing on a cart with wheels and the reservoir and the supply of pressurized air are within the housing.

18. The system of claim 13, wherein the decontamination unit comprises a housing mounted to a wall, and the reservoir and the supply of pressurized air are disposed within the housing.

19. The system of claim 13, wherein the decontamination unit comprises a spring-loaded reel on which an umbilical housing of a respective connector assembly is wound.

20. The system of claim 13, wherein the decontamination unit comprises a power source, and the one or more connector assemblies comprise electrical lines for electrical connection to an electrical component of the system.

* * * * *